United States Patent [19]

Mendelson et al.

[11] Patent Number: 5,552,406
[45] Date of Patent: Sep. 3, 1996

[54] METHOD FOR TREATING PAIN AND BRAIN PERFUSION ABNORMALITIES USING MIXED OPIOID AGONIST-ANTAGONISTS

[75] Inventors: Jack H. Mendelson; Nancy K. Mello, both of Rockport, Mass.

[73] Assignee: The McLean Hospital Corporation, Belmont, Mass.

[21] Appl. No.: 261,770

[22] Filed: Jun. 17, 1994

[51] Int. Cl.$^6$ .......................... A61K 31/56; C07D 489/12
[52] U.S. Cl. ................................................ 514/279; 546/39
[58] Field of Search ............................... 514/279; 546/39

[56]  References Cited

U.S. PATENT DOCUMENTS

| | | | |
|---|---|---|---|
| 3,433,791 | 3/1969 | Bentley et al. | 260/285 |
| 4,464,378 | 8/1984 | Hussain | 424/260 |
| 4,489,079 | 12/1984 | Giudice et al. | 424/260 |
| 4,582,835 | 4/1986 | Lewis et al. | 514/282 |
| 4,956,171 | 9/1990 | Chang | 424/449 |
| 5,026,556 | 6/1991 | Drust et al. | 424/449 |
| 5,069,909 | 12/1991 | Sharma et al. | 424/449 |
| 5,075,341 | 12/1991 | Mendelson et al. | 514/282 |
| 5,240,711 | 8/1993 | Hille et al. | 424/448 |
| 5,240,932 | 8/1993 | Morimoto et al. | 514/282 |

FOREIGN PATENT DOCUMENTS

| | | |
|---|---|---|
| 0069600 | 7/1982 | European Pat. Off. . |
| 0432945 | 11/1990 | European Pat. Off. . |

OTHER PUBLICATIONS

Ascher et al., "Coronary Artery Spasm, Cardiac Arrest, Transient Electrocardiographic Q Waves and Stunned Myocardium in Cocaine–Associated Acute Myocardial Infarction," *Am. J. Cardiol.* 61(11):939–941 (1988).
Barash et al. eds. "Postanasthesia and Consultant Practice," *Clinical Anesthesia,* J. B. Lippincott Co., Publ., Philadelphia, PA, pp. 1449–1450 (1989).
Baron, J. C., "Neuroimaging procedures in acute ischemic stroke," *Current Opinion Neurology* 6:900–904 (1993).
Baskin et al., "Naloxone Reversal and Morphine Exacerbation of Neurologic Deficits Secondary to Focal Cerebral Ischemia in Baboons," *Brain Research* 290:289–296 (1984).
Bickel et al., "Buprenorphine: Dose–Related Blockade of Opioid Challenge Effects in Opioid Dependent Humans[1,2]," *J. Pharm. Exp. Ther.* 247(1):47–53 (1988).
Brass et al., "The Role of Single Photon Emission Computed Tomography Brain Imaging With $^{99m}$Tc–Bicisate in the Localization and Definition of Mechanism of Ischemic Stroke," *J. Cerebral Blood Flow and Met.* 14(Supp. 1):S91–S98 (1994).
Buchweitz et al., "Effect of Morphine on Regional Cerebral Oxygen Consumption and Supply," *Brain Research* 291:301–308 (1984).
Castle et al., "Assessment of an In Situ Rat Intestine Preparation with Perfused Vascular Bed for Studying the Absorption and First–Pass Metabolism of Drugs," *J. Pharmacol. Methods* 14:255–274 (1985).
Crook et al., "The Prevalence of Pain Complaints in a General Population," *Pain* 18:299–314 (1984).

De Roo et al., "Clinical experience with Tc–99m HM–PAO high resolution SPECT of the brain in patients with cerebrovascular accidents," *Eur. J. Nucl. Med.* 15:9–15 (1989).
Dohi et al., "A Mechanism of Morphine–Induced Reduction of Central Nervous System Blood Flow," *No To Shinkei* 35(11):1083–1088 (1983).
Donahoe and Falek, "Neuroimmunomodulation by Opiates and Other Drugs of Abuse: Relationship to HIV Infection and AIDS," in: Psychological, Neuropsychiatric and Substance Abuse Aspects of AIDS, Bridge et al. eds., Raven Press, NY, NY, pp. 145–158 (1988).
Drummond et al., "A Comparison of the Direct Cerebral Vasodilating Potencies of Halothane and Isoflurane in the New Zealand White Rabbit," *Anesthesiology* 65(5):462–467 (1986).
Drummond et al., "The Effect of Nitrous Oxide on Cortical Cerebral Blood Flow during Anesthesia with Halothane and Isofluorane, with and without Morphine, in the Rabbit," *Anesth. Analg.* 66:1083–1089 (1987).
Ferrell et al., "Pain in the Nursing Home," *JAGS* 38(4):409–414 (1990).
Ferrell and Ferrell, "Principles of Pain Management in Older People," *Comprehensive Therapy* 17(8):53–58 (1991).
Forman and Stratton, "Current approaches to chronic pain in older patients," *Geriatrics* 46 (7):47–52 (1991).
Gaines et al., "Effect of Naloxone on Experimental Stroke in Awake Monkeys," *Neurosurgery* 14(3):308–314 (1984).
Gordon, R. S. "From the NIH. Pain in the Elderly: Patterns Change with Age," *JAMA* 241(23):2491–2492 (1979).
Harter and Petersdorf, "Pyogenic Infections of the Central Nervous System," in: Harrison's Principles of Internal Medicine, 11th ed., Braunwald et al., eds., McGraw–Hill, Publ., NY, NY, pp. 1980–1987 (1987).
Helme and Katz, "Management of Chronic Pain," *Med. J. Australia* 158:478–481 (1993).
Hoehner et al., "Effect of Intracarotid and Intraventricular Morphine on Regional Cerebral Blood Flow and Metabolism in Pentobarbital–Anesthetized Dogs," *Anesth. Analg.* 76(2):266–273 (1993).
Holman et al., "Brain Perfusion is Abnormal in Cocaine–Dependent Polydrug Users: A Study Using Technetium–99m–HMPAO and ASPECT," *J. Nuclear Med.* 32(6):1206–1210 (1991).
Holman et al., "Brain Perfusion SPECT Using an Annular Single Crystal Camera: Initial Clinical Experience," *J. Nucl. Med.* 31(9):1456–1461 (1990).
Holman et al., "A Comparison of Brain Perfusion SPECT in Cocaine Abuse and AIDS Dementia Complex," *J. Nucl. Med.* 33(7):1312–1315 (1992).

(List continued on next page.)

*Primary Examiner*—Peter O'Sullivan
*Attorney, Agent, or Firm*—Sterne, Kessler, Goldstein & Fox P.L.L.C.

[57]  ABSTRACT

A method for treating pain and brain perfusion abnormalities using mixed opiate agonist/antagonists is provided.

7 Claims, 1 Drawing Sheet

OTHER PUBLICATIONS

Holman et al., "Regional Cerebral Blood Flow Improves with Treatment in Chronic Cocaine Polydrug Users," *J. Nucl. Med.* 33(5):887 Abstract No. 263 (1992).

Holman et al., "Regional Cerebral Blood Flow Improves with Treatment in Chronic Cocaine Polydrug Users," *J. Nucl. Med.* 34:723–727 (1993).

Hubbard and Sundt, "Failure of naloxone to affect focal incomplete cerebral ischemia and collateral blood flow in cats," *J. Neurosurg.* 59:237–244 (1983).

Johnson et al., "Cerebral Perfusion Imaging in Alzheimer's Disease," *Arch. Neurol.* 44:165–168 (1987).

Kastin et al., "Failure of MIF-1 or Naloxone to Reverse Ischemic-Induced Neurologic Deficits in Gerbils," *Pharmacol. Biochem. Behav.* 17:1083–1085 (1982).

Kaul and Davidow, "Drug Abuse Patterns of Patients on Methadone Treatment in New York City," *Am. J. Drug Alcohol Abuse* 8(1):17–25 (1981).

Kessler et al., "Doppler $CO_2$-test in patients with vertebrobasilar ischemia," *Acta Neurol. Scand.* 84:519–522 (1991).

Kirsch et al., "Effect of Centrally Administered Encephalinamides on Regional Cerebral Blood Flow in the Dog," *J. Cerebral Blood Flow and Metab.* 8(3):385–394 (1988).

Kistler et al., "Cerebrovascular Diseases," in: Harrisons's Principles of Internal Medicine, 11th Ed., Braunwald et al., eds., McGraw-Hill, NY, NY, p. 1930 (1987).

Kobari et al., "Effects of (D–Met$^2$, Pro$^5$)–Enkephalinamide and Naloxone on Pial Vessels in Cats," *J. Cereb. Blood Flow Metab.* 5(1):34–39 (1985).

Kobayashi and Hayashi, "Effect of naloxone on focal cerebral ischemia in cats," *Neurochirurgia* 35:69–73 (1992).

Kosten and Kleber, "Buprenorphine Detoxification From Opioid Dependence: A Pilot Study," *Life Sci.* 42:635–641 (1988).

Kosten et al., "Cocaine Abuse Among Opioid Addicts: Demographic and Diagnostic Factors in Treatment," *Am. J. Drug Alcohol Abuse* 12(1 & 2):1–16 (1986).

Kozel and Adams, "Epidemiology of Drug Abuse: An Overview," *Science* 234:970–974 (1986).

Lau–Ting and Phoon, "Aches and Pains Among Singapore Elderly," *Sing. Med. J.* 29:164–167 (1988).

Law et al., "The effects of acute and chronic morphine on regional distribution of cardiac output in brain," *Experientia* 41:78–80 (1985).

Levin et al., "Public Attitudes Toward Cancer Pain," *Cancer* 56:2337–2339 (1985).

Levy et al., "Effect of Naloxone on Neurologic Deficit and Cortical Blood Flow During Focal Cerebral Ischemia in Cats," *Life Sci.* 31:2205–2208 (1982).

Lewis, J. W., "Ring C–Bridged Derivatives of Thebaine and Oripavine," in: Narcotic Antagonists: Advances in Biochemical Pharmacology, Braude et al., eds., Raven Press, NY, NY, vol. 8, pp. 123–136 (1974).

Lewis et al., "The Pharmacology and Abuse Potential of Buprenorphine: A New Antagonist Analgesic," *Advances in Substance Abuse* 3:103–154 (1983).

London et al., "Cocaine–Induced Reduction of Glucose Utilization in Human Brain," *Arch. Gen. Psychiatry* 47:567–574 (1990).

Matsumiya and Dohi, "Effects of Intravenous or Subarachnoid Morphine on Cerebral and Spinal Cord Hemodynamics and Antagonism with Naloxone in Dogs," *Anesthesiology* 59(3):175–181 (1983).

Mello et al., "Buprenorphine and Naltrexone Effects on Cocaine Self–Administration by Rhesus Monkeys," *J. Pharmacology Exp. Ther.* 254(3):926–939 (1990).

Mello et al., "Buprenorphine Suppresses Cocaine Self–Administration by Rhesus Monkeys," *Science* 245:859–862 (1989).

Mello et al., "The Effects of Chronic Buprenorphine Treatment on Cocaine and Food Self–Administration by Rhesus Monkeys," *J. Pharmacology Exp. Ther.* 260(3):1185–1193 (1992).

Mello et al., "Effects of Intermittent Buprenorphine Administration on Cocaine Self–Administration by Rhesus Monkeys," *J. Pharmacol. Exp. Ther.* 264(2):530–541 (1993).

Mello et al., "Naltrexone–Buprenorphine Interactions: Effects on Cocaine Self–Administration," *Neuropsychopharmacology* 9(3):211–224 (1993).

Mendelson et al., "Buprenorphine Attenuates the Effects of Cocaine on Adrenocorticotropin (ACTH) Secretion and Mood States in Man," *Neuropsychopharmacology* 7(2):157–162 (1992).

Namba et al., "Opiate–Antagonist Reversal of Neurological Deficits—Experimental and Clinical Studies," *Japanese J. Psychiatry and Neur.* 40(1):61–79 (1986).

Phillis et al., "Naloxone Enhances Cerebral Reactive Hyperemia in the Rat," *Neurosurgery* 17(4):596–599 (1985).

Postiglione et al., "Cerebral blood flow in patients with dementia of Alzheimer's type," *Aging Clin. Exp. Res.* 5(1):19–26 (1993).

Roche and Forman, "Pain Management for the Geriatric Patient," *Clinics in Pod. Med. and Surg.* 11(1):41–53 (1994).

Roy and Thomas, "A Survey of Chronic Pain In an Elderly Population," *Can. Fam. Phys.* 32:513–514, 516 (1986).

Sandor et al., "Continuous Measurement of Cerebral Blood Volume in Rats with the Photoelectric Technique: Effect of Morphine and Naloxone," *Life Sci.* 39:1657–1665 (1986).

Scheller et al., "The Effects of Sevoflurane on Cerebral Blood Flow, Cerebral Metabolic Rate for Oxygen, Intracranial Pressure, and the Electroencephalogram are Similar to Those of Isofluorane in the Rabbit," *Anesthesiology* 68(4):548–551 (1988).

Strickland et al., "Long Term Effect of Cocaine Abuse on Brain Perfusion: Assessment with XE–133 rCBF and Tc99m–HMPAO," *J. Nucl. Med.* 32:1021 Abstract No. 474 (1991).

Tatsch et al., "Functional and Morphological Findings in Early and Advanced Stages of HIV Infection: A Comparision of $^{99m}$Tc–HMPAO SPECT with CT and MRI Studies," *Nucl.–Med.* 29:252–258 (1990).

Teoh et al., "Acute Interactions of Buprenorphine with Intravenous Cocaine and Morphine: An Investigational New Drug Phase I Safety Evaluation," *J. Clin. Psychopharmacol.* 13(2):87–99 (1993).

Theodore et al., "The Effect of Naloxone on Cerebral Blood Flow and Glucose Metabolism in Patients with Complex Partial Seizures," *Epilepsy Research* 16:51–54 (1993).

Trusk and Stein, "Effect of Intravenous Heroin and Naloxone on Regional Cerebral Blood Flow in the Conscious Rat," *Brain Research* 406:238–245 (1987).

Tumeh et al., "Cerebral Abnormalities in Cocaine Abusers: Demonstration by SPECT Perfusion Brain Scintigraphy," *Radiology* 176:821–824 (1990).

Turcani et al., "Dual Effect of Naloxone on Blood Platelet Aggregation an Cerebral Blood Flow in Gerbils," *Thromb. Research* 44:817–828 (1986).

Turner et al., "Cerebral and Systemic Vascular Effects of Naloxone in Pentobarbital–anesthetized Normal Dogs," *Neurosurgery* 14(3):276–282 (1984).

Turner et al., "High Dose Naloxone Produces Cerebral Vasodilation," *Neurosurgery* 15(2):192–197 (1984).

Volkow et al., "Cerebral Blood Flow in Chronic Cocaine Users: A Study With Positron Emission Tomography," *Brit. J. Psych.* 152:641–648 (1988).

Volkow et al., "Regional Brain Metabolic Activity During Different Stages of Cocaine Withdrawal," *J. Nucl. Med.* 32:960 Abstract No. 217 (1991).

Weber et al., "SPECT Regional Cerebral Blood Flow (rCBF) Studies in Crack Users and Control Subjects," *J. Nuclear Med.* 31(5):876–877 Abstract No. 728 (1990).

METHOD FOR TREATING PAIN AND BRAIN PERFUSION ABNORMALITIES USING MIXED OPIOID AGONIST-ANTAGONISTS

BACKGROUND OF THE INVENTION

1. Field of the Invention

The present invention relates to a method for treating pain and brain perfusion abnormalities by the administration of mixed opioid agonist-antagonists.

2. Brief Description of the Background Art

Cocaine abuse has reached epidemic proportions in the general population (Kozel, N. J., et al., *Science* 234:970 (1986); and has also increased among heroin-dependent persons, including those in methadone maintenance treatment programs (Kosten, T. R., et al., *Am. J. Drug Alcohol Abuse* 12:1 (1986); Kaul, B., et al., ibid. 8:27 (1981)). The medical and neurological complications associated with cocaine and polydrug abuse are well known. Several studies in the last few years have demonstrated regional abnormalities in cerebral blood flow (rCBF) and metabolism in chronic and acute cocaine use (Holman et at., *J. Nucl. Med.* 33:1312–1315 (1992); Holman et al., *J. Nucl. Med.* 34:723–727 (1993)). For example Tc-99 mHMPAO single photon emission computed tomography (SPECT) has been used to demonstrate focal perfusion abnormalities, especially in interior brain structures, in exclusively cocaine-dependent men, and in cocaine and polydrug dependent men. It has also been reported that the abnormal brain perfusion patterns associated with polydrug and chronic cocaine users are indistinguishable from those in early-AIDS dementia complex (Holman et al., *J. Nucl. Med.* 33:1312–1315 (1992)).

The aforementioned alterations in regional blood flow is attributed to the vasoconstrictive activity of cocaine. Vasoconstriction has been reported in the coronary arteries in association with cocaine administration (Ascher et al., *J. Cardiol.* 61:939–941 (1988)) and cocaine has been reported to cause elevated blood pressure and heart rate as well as focal cerebral lesions such as intracranial or subarachnoid hemorrhage and infarction (Jacobs et al., *Arch. Neurol.* 44:165–168 (1987)).

Chronic cocaine use also results in generalized multifocal alternations in rCBF which occur without underlying structural damage (Volkow et al., *Br. J. Psych.* 152:641–648 (1988); Tumeh et al., *Radiology* 176:821–824 (1990)). A study employing high-resolution imaging techniques detected multiple small and moderate perfusion defects in the cortex, with altered blood flow to the basal ganglia and a generalized reduction in cerebral uptake of radio tracers that distribute proportionately to blood flow (Donahoe et al., *Psychological, Neuropsychiatric and Substance Abuse Aspects of AIDS*, New York, Raven Press, p. 139–143 (1988)). Since most of the patients involved in this study had normal structural findings on CT and MRI scans, the perfusion defects could not be attributed to an underlying infarction and hemorrhage. Moreover, preliminary reports have suggested that these changes in cerebral blood flow are not responsive to short-term withdrawal of drugs and therefore may be a permanent result of cocaine abuse (Strickland et al., *J. Nucl. Med.* 32:1021 (1991); Volkow et al., *J. Nucl. Med.* 32:960 (1991)).

In another study, a substantial improvement in perfusion to cortical areas was observed in cocaine polydrug abusers, with a 45% increase in blood flow after 3–4 weeks of abstention. However, rCBF did not completely return to normal in 9 our of 10 patients tested. While buprenorphine was administered during the period of abstention, it was believed the improvement was due to the abstention, and not the buprenorphine (Holman et al., *J. Nucl. Meal.* 34:723–727 (1993)). These findings of normal structure and partially reversible perfusion abnormalities in cocaine polydrug users support the hypothesis that the observed cortical perfusion defects are due to vasoconstriction, a phenomenon observed in the heart and other organs of cocaine dependent patients (Ascher et al., *Am. J. Cardiol.* 61:931–941 (1988)).

It is also known that opioid, agonist and antagonists, have an adverse effect on cerebral blood flow and metabolism in the normal and ischemic brain. Several groups have reported that opiates, such as morphine or heroine, decrease global or regional CBF after acute administration in normal laboratory animals (Sandor et al., *Life Sci.* 39:1657–1665 (1986); Grandison et al., *Brain Res.* 291:301–308 (1984); Hoehner et al., *Anesth. Analg.* 76:266–273 (1993)). Others have reported similar decreases in cerebral metabolism in dogs (Matsumiya et al., *Anesthesiology* 59:179–181 (1983)) and in chronic polydrug abusing men studied with positron emission tomography (London et al., *Arch. Gen. Psychi.* 47:73–81 (1990)). As mentioned above, cocaine abuse among heroin-dependent subjects has increased, and the abuse of both drags in polydrug dependent patients further compromises cerebral vascular circulation.

The effect of the opioid antagonist naloxone is less clear. Some have shown that it increases rCBF in normal laboratory animal brain (Turner et al., *Neurosurgery* 4:276–282 (1984); Phillis et al., *Neurosurgery* 7:596–609 (1985)), while causing vasodilatation of pial vessels and increasing cerebral blood volume (Turner et al., *Neurosurgery* 15:192–197 (1984); Kobari et al., *J. Cereb. Blood Flow Metab.* 5:34–39 (1985)). It has also been shown in similar models, that naloxone reverses the decrease in CBF caused by morphine, and that it improves CBF in ischemic brain tissue (Hariri et at., *Life Sci.* 39:1657–1665 (1986); Turcani et al., *Thromb. Res.* 44:817–828 (1986)) and improves neurological deficit (Baskin et al., *Brain Res.* 290:289–296 (1984)). However, others have reported the opposite, that it causes a decrement in CBF in normal brain (Turcani et al., *Thromb. Res.* 44:817–828 (1986); Trusk et al., *Brain Res.* 406:238–245 (1987)), that it offers no clinical (Kastin et al., *Pharmacol. Biochem. Behav.* 17:1083–1085 (1982)) or perfusion (Hubbard et al., *J. Neurosurg.* 59:237–244 (1983); Gaines et al., *Neurosurgery* 14:308–314 (1984)) benefit, or actually impairs CBF in ischemic brain (Levy et al., *Life Sci.* 31:2205–2208 (1982)) or that it dangerously increases cerebral metabolism in this injured tissue (Kobayashi et al., *Neurochirurgia* 35:69–73 (1992)).

Another population at risk for brain perfusion abnormalities, and which experiences a disproportionate amount of pain, is geriatric patients. Pain is common in the elderly, occurring in as many as 25–50% of community-dwelling people over age 60 (Ferrel et al., *Comprehensive Therapy* 17(8):53–58 (1991)). It has been shown that the age-associated morbidity of pain is two-fold greater (250/1000 vs 125/1000) in individuals over age 60 compared to individuals less than age 60 (Crook et al., *Pain* 18:299–314 (1984)).

Many painful diseases are, in fact, more common in elderly populations. Arthritis may effect 80% of people over age 65, and most will suffer significant pain. Cancer is also a major contributor to pain syndromes, with more than 60% of cancers occurring in the over-65 age group. Severe pain is present in one-third to one-half of patients undergoing cancer therapy and in more than two-thirds with advanced disease (Levin et al., *Cancer* 56:2337 (1985)). Other specific pain syndromes known to effect the geriatric population disproportionately include herpes xoster, temporal arteritis, polymyalgia rheumatica, and atherosclerotic peripheral vascular disease (Gordon, R. S., *JAMA* 241 (23):2119–2492 (1979)).

Epidemiological studies focusing on nursing home residents reveal that a significant proportion of the "institutionalized" elderly population also suffer from pain syndromes. In the nursing home population, pain reports range from 49%–83% with a predominance of musculoskeletal causes of pain, especially osteoarthritis. It has also been reported that 83% of selected nursing home subjects have a pain "problem" (Roy et al., *Can. Fam. Phys.* 32:513–516 (1986)). In another study of five nursing homes in Singapore it was reported that 39% of the residents had a prevalence of pain (Lau-Tin et al., *Sing. Med. J.* 29:164–167 (1988)).

A study conducted at the Geriatric Research Education and Clinical Center found that 71% of nursing home residents had a pain compliant and 33% of those patients described constant, unrelenting pain. Two-thirds of patients had intermittent pain, 50% of which occurred on a daily basis. Forty percent of subjects complained of low back pain, 38% had arthritis pain of the appendicular skeleton, 14%, pain in a previous fracture site, 11%, neuropathies, 9% had leg cramps and a variety of common pain problems. Pain appeared to directly effect more advanced activities of daily living. Patients often reported difficulty in ambulation and impaired attendance at social activities. Sleep disturbance was also commonly associated with pain among nursing home residents (Farrell et al., *J. Am. Geriatr. Soci.* 38(4):409–414 (1990)).

The geriatric population also suffers from cerebrovascular disease, which is the third leading cause of death after heart disease and cancer in developed countries. In adults, it is the most lethal and disabling of the neurologic diseases. It has an overall prevalence of 794 per 100,000, and 5% of the population over age 65 has at one time in their lives had a stroke. In the United States, it is estimated that more than 400,000 patients are discharged each year from hospitals after a stroke (Petersdoff, et al., eds., *Harrison's Principles of Internal Medicine,* 11th ed., McGraw-Hill, publisher, New York, N.Y., p. 1930 (1987)).

Cerebrovascular insufficiency implicates one or more of the blood vessels of the brain in a pathologic process. The process may be intrinsic to the vessel, as it is in atherosclerosis, or the process may start at a remote site, as occurs when decreased perfusion pressure or increased blood viscosity results in inadequate blood flow through a vessel. Vascular lesions involved in cerebrovascular disease tend to be silent until critical narrowing occurs, which can result in occlusive cerebral disease and ischemia.

SUMMARY OF THE INVENTION

Taking into consideration that a significant proportion of the geriatric population suffers from pain syndromes, and is at risk for brain perfusion abnormalities, a method for the concurrent treatment of these pathologies would have significant therapeutic utility. The present invention provides a method utilizing mixed opioid agonist-antagonists for the treatment of pain experienced by individuals who are at risk for brain perfusion abnormalities.

The present invention is drawn to a method for treating pain and treating or preventing brain perfusion abnormalities in a patient comprising administering to a patient an effective amount of a mixed opioid agonist-antagonist having the following formula:

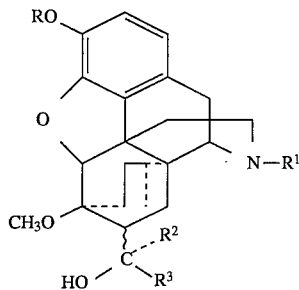

and their non-toxic pharmaceutically-acceptable salts, wherein: the 6,14 bridge-head carbons are bridged by an ethano or etheno group (the dotted line may represent a double bond), R is hydrogen or methyl, $R^1$ is hydrogen, alkyl, alkenyl or alkynyl of up to 8 carbon atoms or cycloalkyl methyl of 4–6 carbon atoms, $R^2$ is hydrogen, alkyl or alkenyl of up to 3 carbon atoms, phenyl or tolyl, and $R^3$ is cycloalkyl of 5–7 carbon atoms, alkyl or alkenyl of up to 8 carbon atoms or alkyl or alkenyl of up to 8 carbon atoms substituted on one of the carbon atoms numbered 1–4 (the carbon atom numbered 1 being adjacent to the carbon atom bearing the alcoholic hydroxy group) by cycloalkyl of 5–7 carbon atoms, phenyl, tolyl, alkoxy of 1–3 carbon atoms, phenoxy or tetrahydrofuryl, provided that in the case where R is hydrogen, $R^2$ and $R^3$ do not contain the system

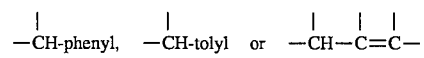

attached directly to the carbon atom bearing the alcoholic hydroxy group.

DETAILED DESCRIPTION OF THE PREFERRED EMBODIMENTS

Figure 1:
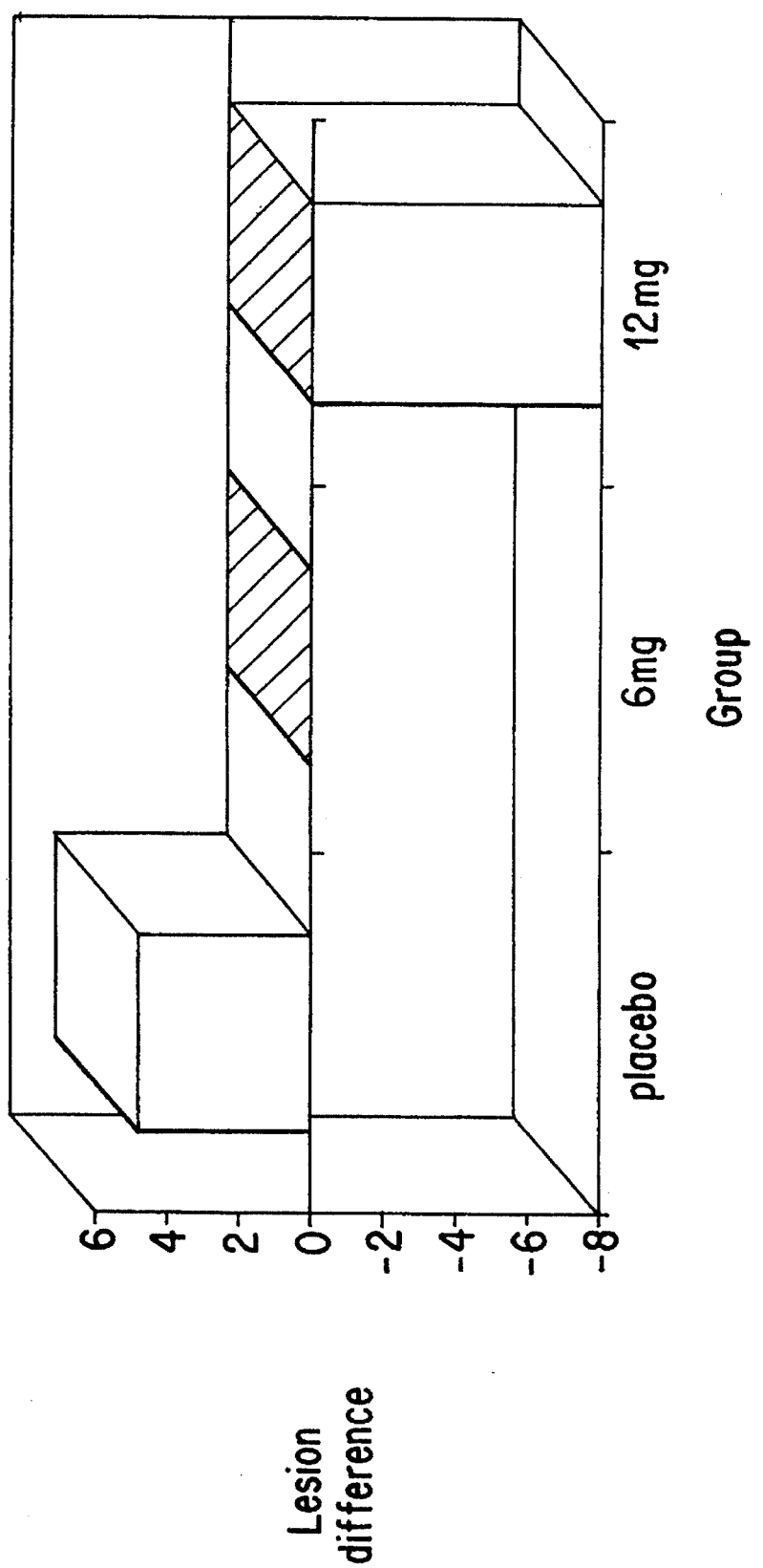
FIG. 1 depicts a bar graph showing the mean difference in lesion count between Study 1 and Study 2, by treatment group. Subjects receiving placebo had an average increase of 4.8±4.7 lesions/study (p=0.008). Comparing doses of buprenorphine, subjects receiving 6 mg had no change (±1.8) in number of lesions/study (p=0.04), while subjects receiving 12 mg had an average decrease of 8±4.6 lesions/study (p=0.002).

In accordance with the present invention, a method for the treatment of pain and/or brain perfusion abnormalities are provided. It has been surprisingly discovered that opioid mixed agonist-antagonist having the following Formula (I):

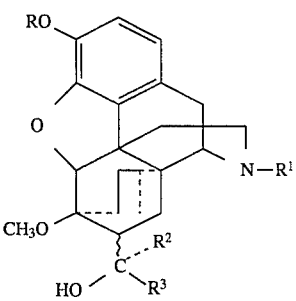

and their non-toxic pharmaceutically-acceptable salts, wherein: the 6,14 bridge-head carbons are bridged by an ethano or etheno group, R is hydrogen or methyl, $R^1$ is hydrogen, alkyl, alkenyl or alkynyl of up to 8 carbon atoms or cycloalkyl methyl of 4–6 carbon atoms, $R^2$ is hydrogen, alkyl or alkenyl of up to 3 carbon atoms, phenyl or tolyl, and $R^3$ is cycloalkyl of 5–7 carbon atoms, alkyl or alkenyl of up to 8 carbon atoms or alkyl or alkenyl of up to 8 carbon atoms substituted on one of the carbon atoms numbered 1–4 (the carbon atom numbered 1 being adjacent to the carbon atom bearing the alcoholic hydroxy group) by cycloalkyl of 5–7 carbon atoms, phenyl, tolyl, alkoxy of 1–3 carbon atoms, phenoxy or tetrahydrofuryl, provided that in the case where R is hydrogen, $R^2$ and $R^3$ do not contain the system

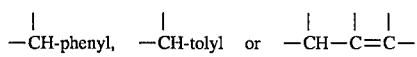

attached directly to the carbon atom bearing the alcoholic hydroxy group, can be utilized to treat pain and treat or prevent cerebral blood perfusion abnormalities.

It was previously believed that abstinence was responsible for improvement in brain perfusion of polydrug users. It has now been discovered that short term abstinence does not improve brain perfusion abnormalities but that mixed opioid agonists-antagonists do. Thus, such mixed opioid agonists-antagonists can be used for the treatment or prevention of brain perfusion abnormalities in population groups susceptible thereto and who are in need of analgesia.

Such mixed opioid agonists-antagonists are disclosed in U.S. Pat. No. No. 3,433,791. Examples include 6,14-endo-ethano-7-(4-hydroxy-4-pentenyl)-tetrahydrothebaine, 6,14-endoethano-7-(1-hydroxy-1-cyclo-hexyl-1-ethyl)-tetrahydrothebaine, 6,14-endoethano-7-(2-hydroxy-1-phenyl-2-propyl)-tetrahydrothebaine, 6,14-endoethano-7-(1-hydroxy-1-phenyl-1-ethyl)-tetrahydrothebaine, N-cyano-6,14-endoethano-7-(2-hydroxy-2-butyl)-tetrahydronorthebaine, N-cyano-6,14-endoethano-7-(2-hydroxy-2-pentyl)-tetrahydronorthebaine, N-cyano-6,14-endoethano-7-(2-hydroxy-3-methyl-2-butyl)-tetrahydronorthebaine, N-cyano-6,14-endoethano-7-(2-hydroxy-2-hexyl)-tetrahydronorthebaine, N-cyano-6,14-endoethano-7-(2-hydroxy-3-methyl-2-pentyl)-tetrahydronorthebaine, N-cyano-6,14-endoethano-7-(2-hydroxy-4-methyl-2-pentyl)-tetrahydronorthebaine, N-cyano-6,14-endoethano-7-(2-hydroxy- 3,3-dimethyl-2-butyl)-tetrahydronorthebaine, N-cyano-6,14-endoethano- 7-(2-hydroxy-2-heptyl)-tetrahydronorthebaine, N-cyano-6,14-endoethano-7-(2-hydroxy-5-methyl-2-hexyl)-tetrahydronorthebaine, N-cyano-6,14-endoethano-7-(1-hydroxy-1-cyclohexyl-1-ethyl)-tetrahydronorthebaine, 6,14-endoethano-7-(2-hydroxy-2-propyl)-tetrahydronorthebaine, 6,14-endoethano- 7-(2-hydroxy-2-butyl)-tetrahydronorthebaine, 6,14-endoethano-7-( 2-hydroxy-2-pentyl)-tetrahydronorthebaine 6,14-endoethano-7-(2-hydroxy-2-hexyl)-tetrahydronorthebaine, 6,14-endoethano-7-(2-hydroxy-4-methyl-2-pentyl)-tetrahydronorthebaine, 6,14-endoethano-7-(2-hydroxy-3,3-dimethyl- 2-butyl)-tetrahydronorthebaine, 6,14-endoethano-7-(2-hydroxy-2-heptyl)tetrahydronorthebaine, N-allyl-6,14-endoethano-7-(2-hydroxy-2-propyl)-tetrahydronorthebaine, N-3,3-dimethylallyl-6,14-endoethano-7-(2-hydroxy- 2-propyl)-tetrahydronorthebaine,N-propargyl-6,14-endoethano-7-(2-hydroxy-2-propyl)-tetrahydronorthebaine, N-cyclopropylmethyl-6,14-endoethano-7-( 2-hydroxy-2-propyl)-tetrahydronorthebaine, N- 7-(2-hydroxy-2-pentyl)-tetrahydronorthebaine, N-cyclopropylmethyl- 6,14-endoethano-7-(2-hydroxy-2-hexyl)-tetrahydronorthebaine, N-cyclopropylmethyl-6,14-endoethano-7-(2-hydroxy- 3,3-dimethyl-2-butyl)-tetrahydronorthebaine, N-cyclopropylmethyl-6,14-endoethano- 7-(2-hydroxy-2-heptyl)-tetrahydronorthebaine, N-cyclopropylmethyl- 6,14-endoethano-7-(1-hydroxy-1-cyclohexyl-1-ethyl)tetrahydronorthebaine, N-cyclopropylmethyl-6,14-endoethano-7-(2-hydroxy-2-propyl)-tetrahydronororipavine, N-cyclopropylmethyl-6,14-endoethano-7-(2-hydroxy-2-hexyl)-tetrahydronororipavine, N-cyclopropylmethyl-6,14-endoethano- 7-(2-hydroxy-3,3-dimethyl-2-butyl)-tetrahydronororipavine.

The mixed opioid agonists-antagonists are virtually devoid of toxic effects during chronic administration. Further, they do not lead to significant physical dependence and their administration can be terminated with minimal withdrawal symptoms.

Of particular interest as an effective pharmacotherapy is buprenorphine (21-cyclopropyl-7α-(2-hydroxy-3,3-dimethyl-2-butyl)-6,14-endo-ethano-6,7,8,14-tetrahydrooripavine). It has been surprisingly discovered that buprenorphine is an excellent pharmacotherapy for treating or preventing brain perfusion abnormalities and pain. This compound is a semi-synthetic, highly lipophilic opioid derived from thebaine which produces analgesia and other CNS effects that are qualitatively similar to those of morphine. While the duration of analgesia may be somewhat longer than with morphine, the subjective and respiratory-depressant effects are unequivocally slower in onset and last longer than those of morphine. Peak miosis occurs about six hours after intramuscular injection, while maximal respiratory depression is observed at about three hours.

Buprenorphine is relatively well absorbed by most routes, with the exception of oral administration, where a significant fraction of the drug is deactivated by the liver. Sublingual administration can be used, and 0.4 to 0.8 mg of the drug given in this manner produces satisfactory analgesia in postoperative patients.

The structure and chemical derivation of this opioid mixed agonist-antagonist have been described by J. W. Lewis in *Narcotic Antagonists: Advances in Biochemical Pharmacology*, M. Braude et al., eds. (Raven, N.Y. 1974), vol. 8, pp. 123–126 and Lewis et al. in *Advances in Substance Abuse, Behavioral and Biological Research*, N. K. Mello, ed. (JAI, Greenwich, Conn., 1983), vol. 3, pp. 103–154.

An "effective amount" of the pharmacotherapies useful for the treatment of pain and brain perfusion abnormalities, including buprenorphine, can be determined using routine clinical evaluations. These evaluations can also be used to determine each compound's relative effectiveness and optimize its dosage. One means available for evaluation is a double-blind (pharmacotherapy versus placebo) trial with randomized patient assignment and objective measures of pain control and brain perfusion parameters. For example, pain can be measured by an artisan using a 10-cm long visual analog scale (VAS) with two anchors; no pain, worst pain imaginable. This method of pain measurement is well-known in the art and has proven to be reliable, valid, and useful in assessing the degree of improvement following intervention. The ischemic tourniquet test can also be used for evaluating the efficacy of analgesic medication. Following mild exercise of an upper extremity under ischemic conditions, time elapsed until pain begins (pain threshold) is determined. The tourniquet remains inflated, and time to patient request to terminate the ischemia (pain tolerance) is measured. The patient is also asked to acknowledge the point when the ischemic pain equals the clinical pain. If the clinical pain is perceived as mild, it will be close to the threshold. If it is severe, it should be close to the tolerance (Barash et al., eds., *Clinical Anesthesia*, J. B. Lippincott Co., publisher, Philadelphia, Pa., p. 1449–14450 (1989)).

Cerebral blood flow can be assessed using Tc-99 m HMPAO single photon emission computed tomography (Holman et al., *J. Nucl. Med.* 34:723–727 (1993)). Cerebral blood flow can also be measured employing positron emission tomography and oxygen-labeled water (Volkow et al., *Brit. J. psych.* 152:641–648 (1988)).

Methods of treatment involve the administration of selected pharmacotherapies in a sufficient dosage to decrease or eliminate the pain while improving brain perfusion. At the same time, the dosage should not be so high to produce any undesirable side effects, such as nausea, vomiting, dizziness, headaches, respiratory depression, etc.

The particular dosage will vary according to the particular compound being administered, the frequency and method of administration, concurrent medication, physical condition and body weight of the subject receiving the dosage, and the like. For the most part, the dosage will range from about 0.4 to 40 mg. Preferably, the dosage will range from about 6 to 24 mg. More preferably the dosage will equal approximately 12 mg. The dosage may be provided in a single dose or alternatively in divided doses.

The present invention comprises a method for treating any animal, including humans, which requires analgesia and will benefit from the treatment or prevention of brain perfusion abnormalities.

In general, the mixed opioid agonists-antagonists of the present invention are available commercially. For example, buprenorphine may be purchased as Buprenex® from suppliers including Norwich Eaton Pharmaceuticals, Inc.

While the mixed opioid agonists-antagonists may be administered as a single agent, it may also be combined with other suitable components to provide a formulation for administration. In this regard, the particular compound may be dissolved in an alcohol or other appropriate solution. Additionally, other pharmacologically acceptable components such as carriers, stabilizers, sugars, buffers, pH adjusters may be included in the formulation.

As noted, buprenorphine is recognized as a particularly effective mixed opioid agonist-antagonist. For use in the present invention, buprenorphine can be administered by any appropriate route, for example, the sublingual, subcutaneous, transdermal, nasal, or intramuscular routes. Generally, buprenorphine doses are more potent when delivered sublingually.

For sublingual administration, buprenorphine is prepared in an appropriate aqueous solution, usually an aqueous ethanol or alcohol solution as provided by Bicket et al., *J. Pharm. Exp. Ther.* 247:47–53 (1988), and Kosten et al., *Life Sci.* 42:635–641 (1988). Additional components, as discussed above, may be included. A sample preparation involves, for example, about 12 mg of buprenorphine dissolved in one ml of a mixture of 95% alcohol (30%) and a titrate phosphate buffer (70%, pH 5). This solution may be prepared and stored for about 2 to 3 weeks in opaque sealed containers.

The prepared solution is administered sublingually in a constant volume of about 1 ml. During administration, the subject is required to hold the solution under his/her tongue for a period of time from about 5 to 20 min, usually about 8 to 12 min.

For subcutaneous administration, the buprenorphine is dissolved in an appropriate aqueous solution and the pH adjusted to approximately 4–6, usually about pH 4.5. The solution is then ready for injection into the subject.

The transdermal delivery of the subject pharmacotherapies can be accomplished in one of several ways as described in U.S. Pat. Nos. 5,026,556, and 5,240,932. For example, as described in U.S. Pat. No. 5,026,556, buprenorphine may be directly applied to the skin suspended or dissolved in a carrier comprising a polar solvent material and a polar lipid material such as propylene glycol and methyl laurate, respectively. The ratio of polar solvent:polar lipid material in such a composition should be approximately 97:3 and contain from about 1.0–40 mg of mixed opioid agonists-antagonists. A similar method for transdermal delivery is described in U.S. Pat. No. 5,240,932. Using this method, the subject mixed opioid agonists-antagonists makes up 1 to 20 weight percent of a percutaneous absorption accelerator comprised of one of (a) a terpene and (b) essential oil; from 10 to 60 weight percent of a percutaneous absorption accelerating assistant comprised of one of (a) a lower alcohol having 1–5 carbon atoms, (b) water and (c) a lower glycol having 2–5 carbon atoms.

Alternatively, the mixed opioid agonists-antagonists used in the claimed method can be administered transdermally via a transdermal adhesive patch. Such patches are well known in the art and generally include a laminated composite device that includes a reservoir layer containing the active compound, with or without a permeation enhancer, a pressure-sensitive adhesive layer for attaching the device to the skin, and an impermeable backing layer. Some examples of suitable adhesive patch devices are described in U.S. Pat. Nos. 4,956,171, 5,069,909 and 5,240,711.

As recited above, the mixed opioid agonists-antagonists used in the disclosed method can also be administered nasally as described in U.S. Pat. No. 4,464,378.

During the duration of treatment described herein, the subjects receiving the treatment can be monitored to determine the overall effect of the pharmacotherapy. In this manner, dosages can be increased or decreased to provide the most effective dosage for a particular subject. Monitoring will include respiratory and pulse rates, blood pressure, temperature, degree of pain control and improvements in brain perfusion abnormalities.

Patient groups that will benefit from the present invention include individuals experiencing pain who are also at increased risk for brain perfusion abnormalities, such as stroke. Examples of which include, but are not limited to, geriatric patients suffering from arthritis, cancer, herpes xoster, temporal arteritis, polymyalgia rheumatica, atherosclerotic peripheral vascular disease, hip or other skeletal fractures, post-operative pain including hip replacement surgery, and osteoporosis. In addition, patients suffering from pain who are also cocaine or polydrug dependent will benefit from this invention.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The above disclosure generally describes the present invention. A more complete understanding can be obtained by reference to the following specific example which is provided herein for purposes of illustration only and is not intended to be limiting unless otherwise specified.

EXAMPLE 1

The Effect of Buprenorphine on Cerebral Perfusion in Drug Abusing Men

Methods

Fifteen men, mean age 33.5 yr. (range 25–45), were enrolled in an inpatient drug abuse treatment center after recruitment by local newspaper advertisements. Each underwent extensive medical and neurological evaluation, with routine blood work, HIV antibody testing, and MRI brain scans. All test results were normal. Drug histories were obtained via: (1) a medical history interview with a physician; (2) written drug history questionnaires; and (3) the orally administered Structured Clinical Interview for DSM-III-R. All subjects met DSM-III-R criteria for cocaine dependence, and all subjects used cocaine intravenously. The subjects reported that they used cocaine for an average of 9.6±5.2 years, and administered an average of 3.8±grams of cocaine per week. All subjects met DSM-III-R criteria for opioid dependence as well, reporting an average of 9.4±6.7 years of abuse and an average of 8.2±5.1 "bags" of heroin administered per day. No subject met DSM-III-R criteria for any other axis I psychiatric diagnosis except for nicotine dependence.

All men were admitted to an inpatient drug treatment research unit. All underwent detoxification with methadone. After detoxification, they were randomly assigned in a double blind fashion to one of three treatment groups: placebo, 6 mg buprenorphine, 12 mg buprenorphine. All medication was administered daily by the sublingual route, and the administration was observed. Doses of medication were increased daily from 1 mg on study day 1 to the maintenance dose mentioned above on day 5. Medication was then maintained at that steady dose from study day 5 until study day 16, at which point it was tapered to zero by study day 21 (however, four patients were maintained on study drug at their request, two receiving 12 mg buprenorphine, one receiving 6 mg buprenorphine, and one receiving placebo.)

Imaging Protocol

Brain perfusion SPECT imaging was performed on three occasions: on study day 1 (Study 1), on study day 5 (Study 2), and on study day 21 (Study 3). All 15 subjects had Study 1 and Study 2. Twelve subjects had Study 3 in addition, and of these, only 2 were among those not tapered off study drug.

Imaging began 10–15 minutes following the intravenous injection of 20 miCi of Tc-99 m HMPAO (Ceretec, Amersham, Ltd., Amersham, England). Data was acquired for 40 minutes on an ASPECT system (digital Scintigraphics, Inc., Boston, Mass.) in 120 projections with a 360° rotation of the collimators. Two pulse-height analyzer windows were employed, one set at 140±14 keV and one set to acquire scatter information from 112–126 keV. The combined set of projections was then calculated by subtracting 90% of the scatter projections and prefiltered to remove the forward scatter component from the photopeak projections using a Butterworth filter (cutoff =1.05 cycles/cm; power facto=20). Data was attenuation-corrected, reconstructed in the axial plane parallel to the orbitometal line and in the coronal plane. The reconstructed slices were displayed on a 128×128 matrix (1.67×1.67 mm pixel size) as a set of 20 5 mm thick axial slices and as a set of 42 1.67 mm thick coronal slices.

Axial magnetic resonance images were acquired using a 1.5 Tesla Signa System (General Electric Co., Milwaukee, Wis.). T1-weighted (TR=600 msec/Te=20 msec), and T-2 weighted and proton density (TR=3000 msec/TE=80,30 msec/nex=0.5) 3 mm thick slices were obtained with a 256×192 matrix and a 24-cm field of view.

Image Analysis

SPECT images were interpreted by three radiologists, each blinded to the identity, the treatment group designation, and the order of each subject's studies. The color display level was individually adjusted for each study so that the central area of the cerebellum was white (greater than 90% of the maximum activity of the slice), thus normalizing the entire study to the Tc-99 m HMPAO activity in the cerebellum. Each study was analyzed for defects (lesions) in perfusion visible on at least two (axial) or three (coronal) contiguous slices. A perfusion defect was defined as an area of at least 0.5 cm in diameter in which total activity was less than 60% of maximum, or where color changed from orange to blue. Defects were considered small if they were between 0.5 and 1 cm in diameter, medium if between 1 and 2 cm, and large if greater than 2 cm in diameter. Total number and size of distinct defects was determined for each region (frontal, temporal, parietal, occipital, basal ganglia, thalamus, and cerebellum) of each study, and recorded on a database.

MR studies were interpreted by a single neuroradiologist also blinded to the treatment group designation of each subject.

Statistical Analysis

Number of defects were treated in a weighted fashion, with small defects receiving a weighting of 1, medium defects a weighting of 2, and large defects a weighting of 3. The number of these weighted defects was then compared across treatment groups (different doses of buprenorphine and placebo) using the Mann-Whitney U test, as were differences in covariates among treatment groups. All tests and reported p values are two-sided. Dispersion about the mean is reported as ±1 standard deviation.

Results

No significant differences were found among the treatment groups with respect to any of the following covariates: age, body mass index (BMI), amount of cocaine and heroin use, duration of cocaine and heroin use, and alcohol use (see Table 1). All MR studies were interpreted as normal.

TABLE 1

|  | Control (n = 5) | 6 mg (n = 5) | 12 mg (n = 5) |
|---|---|---|---|
| Age | 36.2 ± 7.6 | 32 ± 5.1 | 32.2 ± 3.4 |
| BMI | 28.4 ± 8.9 | 24.9 ± 1.9 | 23.8 ± 3.2 |
| Duration of heroin use (yrs) | 7.6 ± 5.9 | 13.4 ± 8.6 | 7.1 ± 4 |
| Amount of heroin use ("bags"/day) | 7.8 ± 2.8 | 11.7 ± 6.6 | 5.2 ± 3.5 |
| Duration of cocaine use (yrs.) | 13.2 ± 4.5 | 8.4 ± 5.3 | 7.3 ± 4.7 |

TABLE 1-continued

| | Control (n = 5) | 6 mg (n = 5) | 12 mg (n = 5) |
|---|---|---|---|
| Amount of cocaine use (grams/week) | 2.95 ± 3 | 7.2 ± 4.6 | 1.3 ± 1 |

No significant difference between any of the groups: Mann-Whiteney U test yields p values > 0.05 for all comparisons.

Comparing the weighted number of defects at baseline (Study 1) and after 5 days of escalating buprenorphine therapy (Study 2), it was found that subjects receiving buprenorphine had an average decrease of 4±5.4 defects/study, while those receiving placebo had an average increase of 4.8±4.7 defects/study (p=0.008). Comparing doses of buprenorphine, subjects receiving 6 mg had no change (±1.8) in number of defects/study (p=0.04), while subjects receiving 12 mg had an average decrease of 8±4.6 defects/study (p=0.002). (See FIG. 1.)

The number of defects at baseline (Study 1) and after tapering off buprenorphine (Study 3) was compared in all except 2 subjects, one of whom was maintained on placebo and the other on 6 mg of buprenorphine. No significant difference was found between subjects who had previously received buprenorphine and those who had previously received placebo (average decrease of 2±7.9 defects/study vs. 1±6 defects/study, p=0.93). Comparing doses of buprenorphine did not affect these results. Those receiving 6 mg having an average increase of 0.6±6.5 defects/study (p=0.54) and those receiving 12 mg having an average decrease of 6.3±9.5 defects/study (p=0.48), as compared to placebo.

Discussion

These results demonstrate that subjects treated with buprenorphine experience a significant decrease in the number of perfusion defects 5 days after beginning treatment, as compared to placebo. These results also indicate that the decrease in perfusion defects was dose related, and that those receiving 12 mg had significantly more reduction in defect number than those receiving 6 rag. As the different dose groups did not significantly differ in terms of number of baseline defects, baseline differences do not underlie the findings.

A comparison of the baseline study (Study 1) with a study following discontinuation of buprenorphine (Study 3), revealed no difference between either dose of buprenorphine and placebo in terms of change from the number of baseline perfusion defects. This indicates that buprenorphine rather than abstinence is responsible for the observed improvement in cerebral perfusion.

The ramifications of augmentation of CBF by mixed opioid agonist-antagonists are many. These compounds can be used to treat brain perfusion abnormalities present in the cocaine and polydrug abusing population. In addition, these compounds are particularly useful as analgesics for the treatment of pain experienced by individuals who are at risk for brain perfusion abnormalities, for example geriatric patients. The compounds employed in the present invention have a therapeutic advantage over analgesics such as morphine, because opioid agonist (and antagonists) either impede regional brain flow or have no effect on existing abnormalities of cerebral perfusion. In contrast, the mixed opioid agonist-antagonists utilized in the present invention are excellent analgesics for elderly individuals who require relief from pain but are also at risk for brain perfusion abnormalities.

The disclosed method can also be used for neuroprotection during ischemia disease, and in acute cerebrovascular disease. This method of treatment can also be utilized in conditions in which cerebrovascular circulation is chronically compromised, both in terms of pain control and as enhancement of cerebral perfusion.

What is claimed is:

1. A method for treating pain and treating or preventing brain perfusion abnormalities in an animal which is at risk for brain perfusion abnormalities comprising administering to said animal an effective amount of a compound having the formula:

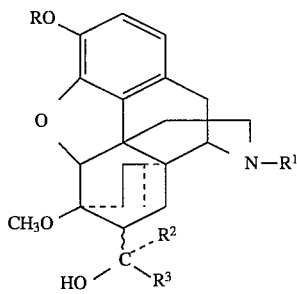

or a non-toxic pharmaceutically-acceptable salt thereof, wherein:
 the 6,14 bridge-head carbons are bridged by an ethano or etheno group,
 R is hydrogen or methyl,
 $R^1$ is hydrogen, alkyl, alkenyl or alkynyl of up to 8 carbon atoms or cycloalkyl methyl of 4–6 carbon atoms,
 $R^2$ is hydrogen, alkyl or alkenyl of up to 3 carbon atoms, phenyl or tolyl, and
 $R^3$ is cycloalkyl of 5–7 carbon atoms, alkyl or alkenyl of up to 8 carbon atoms or alkyl or alkenyl of up to 8 carbon atoms substituted on one of the carbon atoms numbered 1–4 (the carbon atom numbered 1 being adjacent to the carbon atom bearing the alcoholic hydroxy group) by cycloalkyl of 5–7 carbon atoms, phenyl, tolyl, alkoxy of 1–3 carbon atoms, phenoxy or tetrahydrofuryl, provided that in the case where R is hydrogen, $R^2$ and $R^3$ do not contain the system

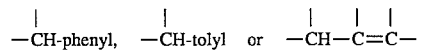

attached directly to the carbon atom bearing the alcoholic hydroxy group.

2. The method of claim 1, wherein said animal is a human geriatric patient.

3. The method of claim 1, wherein said animal is a human age 60 or older.

4. The method of claim 1, wherein said animal suffers from arthritis.

5. The method of claim 1, wherein said compound is administered sublingually.

6. The method of claim 1, wherein said compound is administered subcutaneously.

7. The method of claim 1, wherein said compound is buprenorphine.

* * * * *